(12) United States Patent
Jin et al.

(10) Patent No.: US 10,578,570 B2
(45) Date of Patent: Mar. 3, 2020

(54) TEST SYSTEM OF THERMOELECTRIC MODULE AND TEST METHOD FOR THERMOELECTRIC MODULE

(71) Applicant: HUANENG CLEAN ENERGY RESEARCH INSTITUTE, Beijing (CN)

(72) Inventors: Anjun Jin, Lafayette, CA (US); Dawei Liu, Beijing (CN); Qiming Li, Beijing (CN); Wenbo Peng, Beijing (CN); Shisen Xu, Beijing (CN)

(73) Assignee: Anjun Jin, Lafayette, CA (US)

( * ) Notice: Subject to any disclaimer, the term of this patent is extended or adjusted under 35 U.S.C. 154(b) by 154 days.

(21) Appl. No.: 15/316,901

(22) PCT Filed: Jun. 10, 2014

(86) PCT No.: PCT/CN2014/079614
§ 371 (c)(1),
(2) Date: Dec. 7, 2016

(87) PCT Pub. No.: WO2015/188317
PCT Pub. Date: Dec. 17, 2015

(65) Prior Publication Data
US 2017/0115245 A1    Apr. 27, 2017

(51) Int. Cl.
*G01K 17/00* (2006.01)
*G01K 1/00* (2006.01)
*G01K 7/00* (2006.01)
*G01N 25/20* (2006.01)
*G01R 19/00* (2006.01)
(Continued)

(52) U.S. Cl.
CPC ......... *G01N 25/20* (2013.01); *G01R 19/0092* (2013.01); *G01R 21/133* (2013.01); *G01R 27/02* (2013.01)

(58) Field of Classification Search
USPC .......................................... 374/29, 208, 179
See application file for complete search history.

(56) References Cited

U.S. PATENT DOCUMENTS

2005/0045702 A1* 3/2005 Freeman ............. B23K 1/0016
228/254
2010/0024859 A1* 2/2010 Bell ........................ F01N 5/025
136/201

(Continued)

*Primary Examiner* — Mirellys Jagan (57) ABSTRACT

A test system and method for thermoelectric module. The test system includes an electrical performance test unit, a heat flux detection unit, and a processor. The electrical performance test unit connects with the thermoelectric module under power generation state to test output power of the thermoelectric module and working current and internal resistance under this output power. The heat flux detection unit includes a heat flux sensor installed at a cold-end of the thermoelectric module to detect the heat flux. The processor electrically connects with the electrical performance test unit and the heat flux detection unit to calculate the thermoelectric conversion efficiency η of thermoelectric module. By using the technical scheme of the invention, the detection of the thermoelectric conversion efficiency of the thermoelectric module is accomplished.

14 Claims, 4 Drawing Sheets

(51) Int. Cl.
*G01R 21/133* (2006.01)
*G01R 27/02* (2006.01)

(56) References Cited

U.S. PATENT DOCUMENTS

| | | | |
|---|---|---|---|
| 2010/0071443 A1* | 3/2010 | Wrench | G01N 11/14 73/54.28 |
| 2014/0286373 A1* | 9/2014 | Thresher | G01N 25/18 374/29 |
| 2017/0138646 A1* | 5/2017 | Ihnfeldt | F25B 21/00 |
| 2017/0205364 A1* | 7/2017 | Park | G01N 25/18 |

* cited by examiner

TEST SYSTEM OF THERMOELECTRIC MODULE AND TEST METHOD FOR THERMOELECTRIC MODULE

CROSS-REFERENCE TO RELATED APPLICATIONS

This application is a national phase application of and claims priority to PCT Application No. PCT/CN2014/079614, filed Jun. 10, 2014, and incorporated by reference herein for all purposes.

TECHNICAL FIELD

The invention relates to field of thermoelectric module testing, and more specifically, relates to both a test system and a test method of thermoelectric modules.

BACKGROUND OF THE INVENTION

The existing test system can only test the electrical output performance of thermoelectric module under certain temperature condition, and the thermoelectric conversion efficiency cannot be obtained.

When a thermoelectric module operates, its mechanical (clamping) pressure can affect its performance. The thermoelectric module operates differently depending upon its most suitable pressure settings. This is an important but often overlooked factor. The existing test equipment usually has preset clamping pressure/force.

The parallelism of the upper and lower contact surfaces of thermoelectric module will bring a great influence on their thermal contact, which will determine the accuracy of temperature measurement results. The existing testing equipment generally regulates the parallel degree through multiple spring pressurization which is a relatively passive method and the precision of the parallelism cannot be controlled.

The existing test equipment generally employs water cooling means; the lowest test temperature at the cold-end usually can be controlled only about 10 degrees above the room temperature.

BRIEF SUMMARY OF THE INVENTION

The current invention aims to provide a test system of thermoelectric module and a test method of thermoelectric module to measure the thermoelectric conversion efficiency of thermoelectric module.

In order to achieve the goal, this invention provides a test system of thermoelectric module, the test system includes: an electrical performance test unit, the electrical performance test unit electrically connects with the thermoelectric module which is under power generation state, to measure output power P of the thermoelectric module and working current I and internal resistance R under this output power; a heat flux detection unit, the heat flux detection unit includes the heat flux sensor which is installed at a cold-end of the thermoelectric module to detect a heat flux $Q_{c1}$ at the cold-end; and a processor, the processor electrically connects with the electrical performance test unit to receive information detected by the electrical performance test unit. The processor also electrically connects with the heat flux detection unit to receive the heat flux $Q_{c1}$ at the thermoelectric module cold-end. The processor calculates the thermoelectric conversion efficiency $\eta$ of thermoelectric module according to the formula $\eta=P/(Q_{c1}+P-1/2I^2R)$.

In another embodiment, the heat flux detection unit includes multiple heat flux sensors located in the same plane. The multiple heat flux sensors are all rectangular-shaped heat flux sensors. In an embodiment, a first symmetry axis of the thermoelectric module is parallel with two opposing length edges of each of the multiple heat flux sensors. The multiple heat flux sensors are mirror symmetrically disposed with their lengths in parallel at two sides with respect to the first symmetry axis. along the direction perpendicular to the first symmetry axis, the farther the location of one of multiple heat flux sensors, the longer the length of the one of multiple heat flux sensors.

Further, the thermoelectric module also has a second symmetry axis which is perpendicular to the first symmetry axis, the multiple heat flux sensors are all symmetrically disposed with respect to the second symmetry axis.

Further, the test system of the thermoelectric module also includes a test platform used to set the thermoelectric module up for testing. The test platform includes a first temperature control unit including a first plane and a second temperature control unit including a second plane. The thermoelectric module is loaded between the first plane and the second plane, of which the heat flux sensor is disposed between the first plane and the thermoelectric module.

Further, a first through-hole existed on the second temperature control unit. An opening of the first through-hole is set at the second plane. The test platform also includes the optical fiber set through the first through-hole.

Further, the test platform also includes: a support plate on which the first temperature control unit is arranged, and a first heat insulating material layer arranged between the supporting plate and first temperature control unit.

Further, the test platform also comprises a heat insulating material; the heat insulating material being arranged around the heat flux sensor and thermoelectric module.

Further, the test platform also includes a thermal conductive material plate disposed on the first plane. The thermal conductive material plate includes a first surface facing the first plane and a second surface deviating from the first plane. The second surface includes a containing groove which is matched with heat flux sensor in size.

Further, the second temperature control unit is controllably movable in the direction perpendicular to the first plane with respect to the first temperature control unit.

Further, the test platform also includes a driving unit to drive the second temperature control unit moving along the direction perpendicular to the first plane. The driving unit includes: a fixture part including a horizontal member having a threaded hole and two vertical members having guide rails fixedly set with respect to the first temperature control unit. A driving screw is configured to have a thread-in motion for causing a motion of the second temperature control unit towards the first temperature control unit. The driving screw rod is matched with the threaded hole. The screw rod has a driving mechanism in connection with the second temperature control unit.

Further, the test platform uses the driving unit to drive the second temperature control unit moving along the direction perpendicular to the first plane via a transmission part. The transmission part transfers the power of the driving unit to the second temperature control unit. The transmission part includes a first moving plate connected with the driving unit through a bearing and a second moving plate elastically connected with the first movable plate and coupled with the second temperature control unit.

Further, the vertical member includes a guide section including slide rails for pulley which connects with the first moving plate. The slide rails is oriented in consistent with the moving direction of the second temperature control unit. The slide rails and the pulley are suitably set up to support the relative motion of the pulley therein.

Further, the test platform also includes a second heat insulating material layer installed between the second moving plate and the second temperature control unit.

Further, there is a second through-hole on the first moving plate. The transmission part also includes a connecting screw passing through the second through-hole to connect with the second moving plate. A spring is set on the connecting screw and located between the first moving plate and the second moving plate.

Further, the transmission part includes a plurality of connecting screws.

Further, the inner diameter of the second through-hole is bigger than the outer diameter of the connecting screw. A threaded hole matched with the connecting screw is set on the second moving plate.

Further, the test system also includes a heat flux guide unit which is set between a cold-end of the thermoelectric module and the first plane.

Further, the heat flux guide unit includes a heat conducting sheet installed between the cold-end of the thermoelectric module and the heat flux sensor and a first heat insulation plate having a containing hole. The heat conducting sheet is disposed in the containing hole set in the first heat insulation plate.

Further, the heat conducting sheet is installed between the cold-end of the thermoelectric module and the heat flux sensor. The first heat insulation plate is set between the thermoelectric module and the heat flux sensor. A containing groove is set on the first heat insulation plate. The heat conducting sheet is arranged in the containing groove.

Further, the heat conducting sheet in the containing groove is set on the surface of the first heat insulation sheet with back to the thermoelectric module.

Further, the heat flux guide unit also includes a heat conducting plate arranged between the first plane and the first heat insulation plate. The heat flux sensor is set between the heat conducting plate and the heat conducting sheet.

Further, the heat flux guide unit also includes a second heat insulation plate which is arranged between the first heat insulation plate and the heat conducting plate. The second heat insulation plate includes containing through-hole matched with the heat flux sensor in size.

Further, the containing groove is set on the surface of the heat conducting plate towards the heat conducting plate to accommodate the heat flux sensor.

Further, the depth of the containing groove is less than the thickness of the heat flux sensor; the heat flux guide unit also includes the second heat insulation plate which is arranged between the first heat insulation plate and the heat conducting plate. The containing through-hole matched with the heat flux sensor is set on the second heat insulation plate in order to accommodate the part of the heat flux sensor which is higher than the containing groove of the sensor.

The invention also provides a test method of the thermoelectric module. The test method includes using the above test system of the thermoelectric module to test the performance of the thermoelectric module.

Further, the test method comprises a method for providing a thermoelectric conversion efficiency including the following steps: S1: Measure the output power P, current I, inner resistance R and the cold-end heat flux $Q_{c1}$ of the thermoelectric module under a power generation state; S2: determine the heat flux $Q_h$ at the hot-end of the thermoelectric module, $Q_h=Q_{c1}+P-I^2R/2$; S3: calculate the thermoelectric conversion efficiency $\eta$, $\eta=P/Q_h$.

Further, the output power P is the maximum output power of the thermoelectric module.

Further, the test method also comprises a method for measuring cooling capacity including the following steps: S1: Control the hot-end temperature $T_h$ and the cold-end temperature $T_c$ of the thermoelectric module under refrigeration working state; S2: Measure the heat flux $Q_{c2}$ at the cold-end of the thermoelectric module.

Further, the test method comprises a method for determining cooling capacity by controlling the hot-end temperature $T_h$ and the cold-end temperature $T_c$ of the thermoelectric module under a refrigeration working state, and making $T_h=T_c$, then measuring the heat flux $Q_{c2}$ at the cold-end of the thermoelectric module.

Further, the method includes changing the refrigeration current of the thermoelectric module under the refrigeration working state several times, and measuring the corresponding heat flux $Q_{c2}$ at the cold-end of the thermoelectric module in each of the refrigeration current, and then drawing the relationship curve between the cooling current and the heat flux $Q_{c2}$ at the cold-end of the thermoelectric module, from which a maximum value of the heat flux $Q_{c2}$ in the curve is determined to be the cooling capacity of the thermoelectric module.

Put into use the technical scheme of the invention, the test system includes: an electrical performance test unit, a heat flux detection unit, and a processor. The electrical performance test unit electrically connects with a thermoelectric module, which is under power generation state, to test the output power of the thermoelectric module and the working current and internal resistance under this output power. The heat flux detection unit includes one or more heat flux sensors installed at the cold-end of the thermoelectric module to detect the heat flux at the cold-end. The processor electrically connects with the electrical performance test unit to receive information detected by the electrical performance test unit. The processor also electrically connects with the heat flux detection unit to receive the heat flux $Q_{c1}$ at the thermoelectric module cold-end which is detected by the heat flux detection unit. The processor calculates the thermoelectric conversion efficiency $\eta$ of thermoelectric module according to the formula $\eta=P/(Q_{c1}+P-1/2I^2R)$. By using the technical scheme of the invention, the detection of the thermoelectric conversion efficiency of the thermoelectric module is realized.

BRIEF DESCRIPTION OF THE DRAWINGS

The description of the drawings constituting part of the application is used to provide further understanding of the invention; the schematic embodiments and the corresponding illustrations are used to explain the invention, and do not constitute the improper limit of the invention. In the drawings.

DRAWING REFERENCES

1, electrical performance test unit; 2, thermoelectric modules; 3, processor; 41, the first temperature control unit; 42, second temperature control unit; 43, heat insulation materials; 44, heat conducting material plate; 461, fixed parts; 462, driving screw; 463, transmission part; 4631, first moving plate; 4632, second moving plate; 4633, connecting screw; 4634, spring; 47, support plate; 481, pulley; 5, heat flux sensor; 6, heat flux guide unit; 61, heat flux conducting sheet; 62, first heat insulation plate; 63, heat conducting plate; 64, second heat insulation plate.

DETAILED DESCRIPTION OF THE INVENTION

It should be noted that, in the case of non-conflict, the embodiments in this application and the characteristics of the embodiments can combine with each other. The following will refer to the attached figures and combine with the embodiment to explain the invention in detail.

First Embodiment

As shown in FIGS. 1 to 4, the embodiment of this invention provides a test system of the thermoelectric module, the test system includes the electrical performance test unit 1, heat flux detection unit and processor 3.

Figure 1:
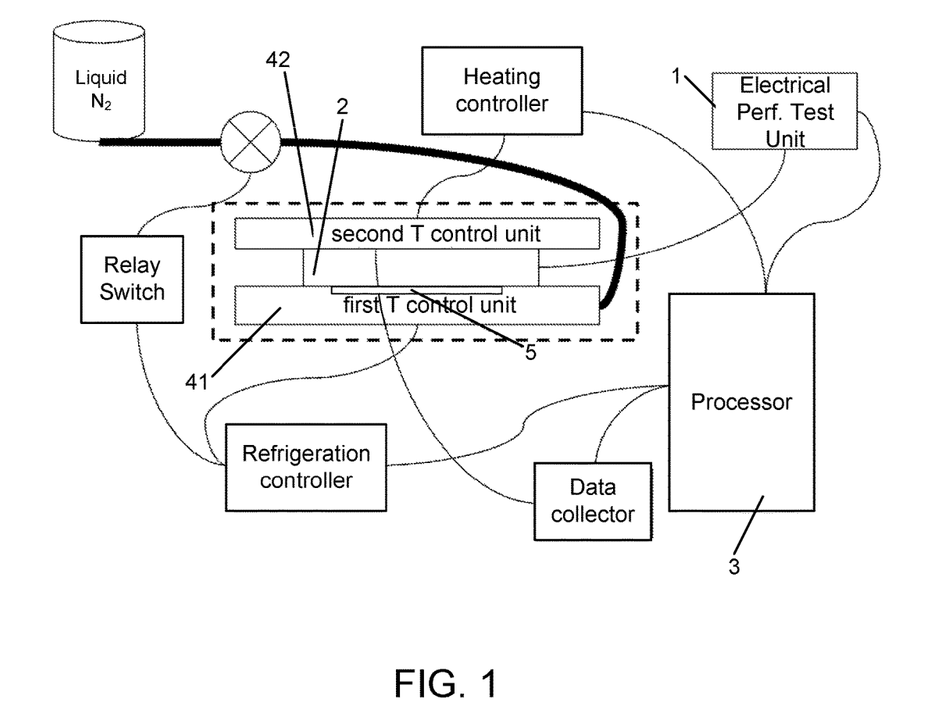
FIG. 1 shows the structure schematic diagram of the test system of the thermoelectric module of the first embodiment of the invention.

Electrical performance test unit 1 electrically connects with the thermoelectric module 2 which is under power generation state to test the output power P of the thermoelectric module 2 and the working current I and internal resistance R under this output power. Heat flux detection unit includes the heat flux sensor 5 which is installed at the cold-end of the thermoelectric module to detect the heat flux $Q_{c1}$ at the thermoelectric module cold-end. Processor 3 electrically connects with the electrical performance test unit 1 to receive the message detected by the electrical performance test unit 1. The processor 3 electrically connects with the heat flux detection unit to receive the heat flux $Q_{c1}$ at the thermoelectric module 2 cold-end which is detected by the heat flux detection unit. The processor 3 calculates the thermoelectric conversion efficiency η of thermoelectric module 2 according to the formula $\eta = P/(Q_{c1}+P-1/2I^2R)$.

The existing test system usually can only test the electrical output performance of thermoelectric module under certain temperature condition, and the thermoelectric conversion efficiency cannot be obtained. In order to compensate for the lack of the existing technology, the embodiment provides a test system of thermoelectric module which can measure the thermoelectric conversion efficiency of the thermoelectric module.

When using the test system of the thermoelectric module in this embodiment to test the thermoelectric conversion efficiency of the thermoelectric module, first, the temperature at the cold-end and hot-end of the thermoelectric module should be controlled at stable temperature at first. Then the thermoelectric conversion efficiency of the thermoelectric module can be measured by using the following test method:

S1: Measure the output power P, current I, inner resistance R and the cold-end heat flux $Q_{c1}$ of the thermoelectric module under power generation state;

S2: Obtain the heat flux $Q_h$ at the hot-end of the thermoelectric module:

$$Q_h = Q_{c1} + P - I^2 R/2;$$

S3: Calculate the thermoelectric conversion efficiency $\eta = P/Q_h$.

Preferably, the output power P is the maximum output power of the thermoelectric module.

Figure 5:
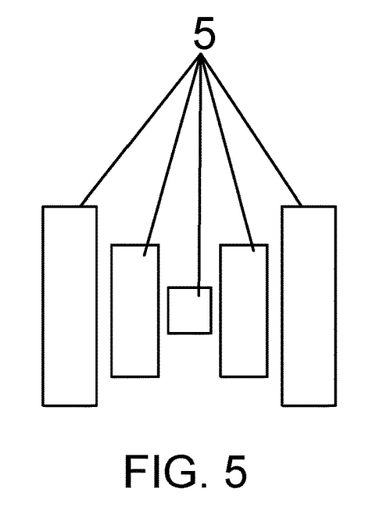
FIG. 5 shows the arrangement mode of the numerous heat sensors of the first embodiment of the invention.

This embodiment provides an arrangement mode of the heat flux sensor. Heat flux detection unit includes multiple heat flux sensors 5 located in the same plane, the multiple heat flux sensors 5 are all rectangular heat flux sensor, the first symmetry axis of the thermoelectric module 2 is parallel with the two relative length edges of the heat flux sensor, the multiple heat flux sensors 5 are symmetrically set with respect to the first symmetry axis, along the direction perpendicular to the first symmetry axis, the farther the location of one of multiple heat flux sensors 5, the longer the length of the one of multiple heat flux sensors 5.

The thermoelectric module 2 also has the second symmetry axis which is perpendicular to the first symmetry axis, the multiple heat flux sensors 5 are all symmetrically set with respect to the second symmetry axis.

FIG. 5 provides the arrangement mode of multiple heat flux sensors in the embodiment of this invention: a 10×10 mm heat flux sensor is arranged at the central, at its left and right sides separately arrange a 30×8 mm heat flux sensor with 2 mm interval. Then at the sides of the two 30×8 mm heat flux sensors far from 10×10 mm heat flux sensor separately arrange a 50×8 mm heat flux sensor with 2 mm interval. This arrange mode can measure the thermoelectric mode with sides more than 10 mm, only the central 10×10 mm heat flux sensor is used for the thermoelectric mode with 10-12 mm side length; 10×10 mm heat flux sensor and two 30×8 mm heat flux sensors are used when the side length of the thermoelectric mode is 12-20 mm. All heat flux sensors are used when the side length of the thermoelectric mode is more than 20 mm. When calculate the total heat flux, the assumption that the distribution center of the heat flux density is symmetrical is needed to be based, so the total heat flux density $W = (W_a + W_b \times 8 + W_c \times 16)/25$. Among them, $W_a$, $W_b$, and $W_c$, were the average heat flux density measured by 10×10 mm, 30×8 mm, and 50×8 mm heat flux sensor respectively.

The arrange mode of multiple heat flux sensors in this embodiment can use limited heat flux sensors to finish the test of various types of thermoelectric module, make good use of the heat flux sensor, and reduce the cost of the testing system.

Figure 2:
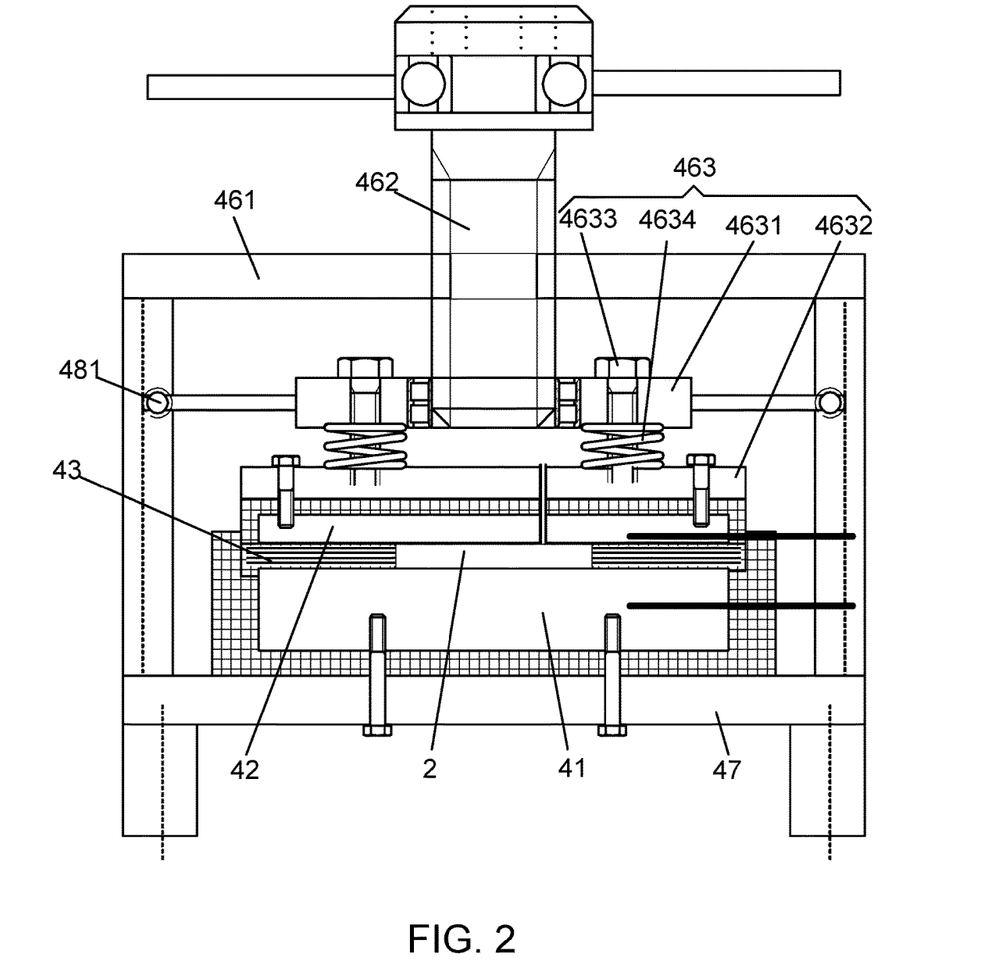
FIG. 2 shows the structure schematic diagram of the test platform of the first embodiment of the invention.

The test system of the thermoelectric module also includes the test platform used to set the thermoelectric module, and the test platform includes the first temperature control unit 41 and the second temperature control unit 42. The first temperature control unit includes a first plane. The second temperature control unit includes a second plane. The thermoelectric module 2 is disposed between the first plane and the second plane. The one or more heat flux sensors 5 are disposed between the first plane and the thermoelectric module 2.

In this embodiment, the first temperature control unit 41 is a cooling plate. The cooling plate includes a shell and heat exchange pipe set in the shell. The first plane of the first temperature control unit is formed on a outer surface of the shell. The test platform also includes a heat exchange medium storage tank, a connecting pipe, an electronic valve, a first temperature sensor, and a refrigeration controller. Heat exchange medium in the heat exchange medium storage tank is liquid nitrogen, though other type of material like water can be an alternative option. The heat exchange medium storage tank is liquid nitrogen bottle connected with the heat exchange pipe in the cooling plate by the connecting pipe. The electronic valve is set on the connecting pipe. The first temperature sensor electrically connects with the refrigeration controller. The first temperature sensor is used to detect the temperature of the cooling plate and transmit the temperature information of the cooling plate to the refrigeration controller. Refrigeration controller electrically connects via a relay switch to control the electronic valve. Refrigeration controller, according to the temperature information of the cooling plate detected by the first temperature sensor, controls the on-off of the electronic valve, so as to realize the control of the temperature of the cooling plate.

The second temperature control unit 42 is a heating temperature control plate. The test platform also includes a heating unit for providing a heat source for the heating temperature control plate. A second temperature sensor and a heating controller are used for detecting the temperature of the second temperature control unit 42. The heating controller, according to the temperature of the second temperature control unit 42 detected by the second temperature sensor, controls the heating work of the heating unit, so as to realize the temperature control of the second temperature control unit.

In this embodiment, the refrigeration controller and the heating controller are electrically connected with the processor 3 to exchange information. The information is transferred to the processor by the refrigeration controller when the first temperature sensor detects the temperature of the first temperature control unit reaches the preset temperature value. The information is transferred to the processor by the heating controller when the second temperature sensor detects the temperature of the second temperature control unit 42 reaches the preset temperature value. When the temperature of the first temperature control unit 41 and the second temperature control unit 42 all reach respective preset values, the processor according to the information detected by the electrical performance test unit 1 and the heat flux detection unit, calculates the thermoelectric conversion efficiency of the thermoelectric module.

A first through-hole is provided on the second temperature control unit 42, an opening of the first through-hole is set at the second plane, and the test platform also includes the optical fiber disposed through the first through-hole.

In order to make the cold-end and the hot-end of the thermoelectric module closely in contact with the first temperature control unit 41 and the second temperature control unit 42 respectively to fully exchange heat. After pre-pressing the thermoelectric module, the parallelism of the first plane, the second plane and the thermoelectric module need to be adjusted. In order to detect the parallelism between the second surface and the thermoelectric module, a piece of glass fiber end is inserted into the first through-hole, and the other end aims to the luminous objects such as a flashlight. If the second plane and the thermoelectric module are not parallel, then it can be observed that light is emitted from the gap of the contact surface. Then it is necessary to adjust the relative position of the horizontal regulating screw until the emitted light from below cannot be observed.

The test platform also includes a support plate 47 and a first heat insulating material layer. The first temperature control unit 41 is arranged on the support plate 47. The first heat insulating material layer is arranged between the supporting plate 47 and first temperature control unit 41.

Preferably, the first heat insulating material also includes a part which surrounds side regions of the first temperature control unit 41.

The first temperature control unit 41 is arranged on the supporting plate 47, and the insulating materials, such as asbestos, are arranged between them. Refrigeration heat exchange medium can use water or liquid nitrogen. The heat transfer power is changed by adjusting the flow rate of the refrigeration heat exchange medium pumped into the refrigeration board, and the temperature at the cold-end of the thermoelectric module is controlled. The connecting pipe of the first temperature control unit 41, the first temperature sensor (thermocouple), and the wire of the heat flux sensor are led through the first heat insulation material layer.

General thickness of the commercial thermoelectric module is 3~5 mm, part of the thickness of the micro thermoelectric module is even less than 1 mm. The smaller distance between the first surface of the first temperature control unit and the second plane of the second temperature control unit is, the more significant the amount of the radiation heat transfer will be, which brings large errors to the heat flux measurement and even leads to be unable to establish the required temperature gradient.

In an embodiment, the test platform of the present disclosure also comprises a heat insulating material 43 arranged around the heat flux sensor 5 and thermoelectric module 2. Preferably, the heat insulating material 43 is composite material with high infrared reflection and thermal insulation.

In this embodiment, by arranging the composite material with high infrared reflection and thermal insulation between the first plane and the second plane to reduce the heat transfer between the first temperature control unit and the second temperature unit.

The material with high infrared reflection and thermal insulation can be chosen from a multilayer composite material of aluminum foil and glass fiber cloth which is composited by a layer of aluminum foil and a layer of glass fiber cloth alternately arranged. The metal foil has high infrared reflection. According to calculation, multiple layers can reduce the influence of infrared radiation heat leakage to negligible extent. Glass fiber has low thermal conductivity with some air in the interval, which can significantly reduce the influence of the heat leakage loss in heat conduction.

Figure 3:
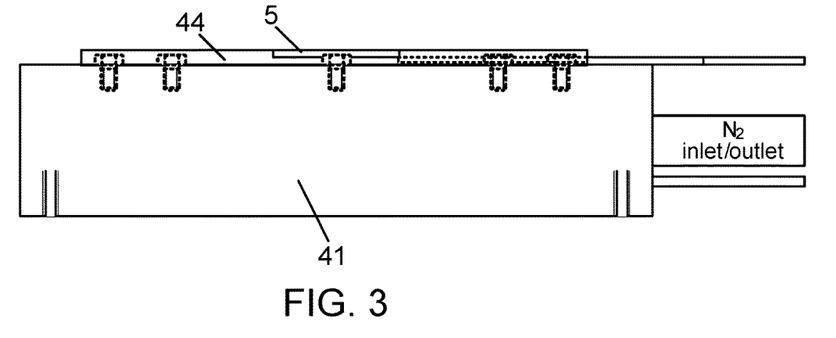
FIG. 3 shows the assembly structure schematic diagram of the first temperature control device, the heat conducting material plate and the heat flux sensor of the first embodiment of the invention.
Figure 4:
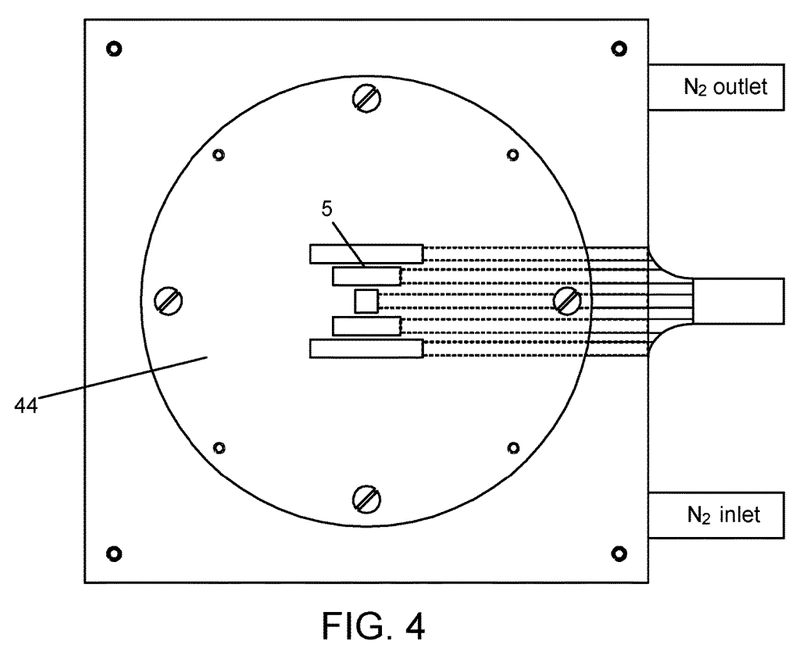
FIG. 4 shows the top view of FIG. 3.

The test platform also includes a thermal conductive material plate 44 disposed on the first plane. The thermal conductive material plate 44 includes a first surface facing towards the first plane and a second surface deviating from the first plane. There is a containing groove in the second surface which is matched with heat flux sensor 5 in size (and shape).

Preferably, the heat conducting material plate is a copper plate.

As shown in FIG. 3 and FIG. 4. In this embodiment, the heat flux sensor is arranged by a copper plate of 5-10 mm thickness. The copper plate is fixed on the first plane of the first temperature control unit 41 by countersunk screws, and the positioning threaded hole is used for assembling high infrared reflection heat insulation composite material. The heat flux sensor is a kind of sensor which can test heat flux. The heat flux sensor is installed on the copper plate by half-buried way. The wires of the heat flux sensor are led from below the copper plate.

The second temperature control unit 42 is designed to be controllably moveable in the direction perpendicular to the first plane with respect to the first temperature control unit 41.

The second temperature control unit 42 is designed to be controllably moveable with respect to the first temperature control unit 41 to clamp the thermoelectric module between the first plane and the second plane.

The test platform also includes a driving unit to drive the second temperature control unit 42 moving along the direction perpendicular to the first plane. The driving unit includes a fixture part with a horizontal member 461 and a driving screw 462. The horizontal member 461 is fixed set via two vertical members to the first temperature control unit 41. A threaded hole is arranged on the horizontal member 461. The threaded-in direction of the driving screw 462 is consistent with the moving direction of the second temperature control unit 42, the driving screw rod 462 is matched with the screw pitch of the thread hole. The screw rod 462 has a driving connection with the second temperature control unit 42.

The size of the threaded hole is determined by the maximum clamping force. For example, 800 kg maximum clamping force requires the diameter of threaded hole over than 50 mm. The size of the thread pitch has relationship with the accuracy of the driving screw 462 moving along the threaded-in direction of the driving screw 462, such as the thread of 0.5 mm pitch size can control the error of vertical feed less than 10 μm. In general, the vertical accuracy of more than 5 microns is completely enough for the test of vast majority thermoelectric module.

The test platform uses the driving unit to drive the second temperature control unit 42 moving along the direction perpendicular to the first plane via a transmission part 463. The transmission part 463 is used to transfer the power of the driving unit to the second temperature control unit 42. The transmission part 463 includes a first moving plate 4631 and a second moving plate 4632.

The first moving plate 4631 connects with the driving unit through bearing. The second moving plate 4632 elastically connects with the first moving plate 4631, the second moving plate 4632 is in contact with the second temperature control unit 42.

The end region of the driving screw rod 462 is connected via the bearing with the first moving plate 4631 for transmitting the pressure from the driving screw rod to the first moving plate 4631. Compared with the direct contact with the first moving plate, the application of the bearing can effectively eliminate the influence of the friction force, thereby increasing the accuracy of the clamping force. Compared with the rigid connection of the upper plate, the rotation of the whole transmission mechanism can be avoided, thereby reducing the difficulty of the whole design and the requirement of processing precision.

The test platform also includes a guide section built in each of the two vertical members fixed with the first temperature control unit 41. The guide section includes a pulley 481 and a slide rail in the vertical member. The pulley 481 connects with the first moving plate 4631. The orientation of the slide rails is consistent with the moving direction of the second temperature control unit 42, the slide rails and the pulley 481 suitably set up to support the motion of the pulley along the slide rail.

The test platform also includes a second heat insulating material layer installed between the second moving plate 4632 and the second temperature control unit 42.

Preferably, the second heat insulating material also includes a part surrounded the second temperature control unit 42. The loss of heat is reduced effectively, and the utilization rate of heat is improved.

There is a second through-hole placed in the first moving plate 4631. The transmission part 463 also includes connecting screws 4633 and springs 4634. Each connecting screw 4633 passes through the second through-hole and connects with the second moving plate 4632. Correspondingly, each spring 4634 is set on the connection screw 4633 and located between the first moving plate 4631 and the second moving plate 4632.

In this embodiment, the transmission part 463 includes a plurality of connecting screws 4633 and a plurality of springs 4634 arranged corresponding to the screws respectively. By rotating each connecting screw 4633, the spring correspondingly set to the connecting screw can be adjusted, so that the parallelism between the second moving plate and the second moving plate can be adjusted.

In an alternative embodiment, a method is provided using the test system of the thermoelectric module according to the disclosure to measure the cooling capacity of the thermoelectric module. The method for measuring cooling capacity includes the following steps:

S1: Control the hot-end temperature $T_h$ and the cold-end temperature $T_c$ of the thermoelectric module under refrigeration working state;

S2: Measure the heat flux $Q_{c2}$ at the cold-end of the thermoelectric module.

The method comprises a cooling capacity testing method, control the hot-end temperature $T_h$ and the cold-end temperature $T_c$ of the thermoelectric module under refrigeration working state, and make $T_h=T_c$, then measure the heat flux $Q_{c2}$ at the cold-end of the thermoelectric module.

According to a theory, the expression of thermoelectric cooling capacity $Q_c$ can be expressed as: $Q_{c2}=\alpha_{NP}T_C I - \frac{1}{2}I^2 R - k(T_h - T_c)$ Among this, $\alpha_{NP}$ is the Seebeck coefficient, $T_h$ and $T_c$ are the temperature at hot-end and cold-end, I is the current, R is the resistance, K is the thermal resistance of the thermoelectric module. It can be seen that the theoretical maximum cooling capacity can be reached when the cold-end and hot-end temperature of the thermoelectric module is the same. The temperature of the first temperature control unit 41 and the second temperature control unit are set to the same temperature during testing, that is, the maximum cooling capacity test temperature.

By changing the refrigeration current of the thermoelectric module under refrigeration working state several times, and measuring the corresponding heat flux $Q_{c2}$ at the cold-end of the thermoelectric module in each of the refrigeration current, a relationship curve between the cooling current and the heat flux $Q_{c2}$ at the cold-end of the thermoelectric module can be plotted. As a result, a maximum value of the heat flux $Q_{c2}$ in the curve is determined to be the maximum cooling capacity of the thermoelectric module.

It can be seen from the formula that, when the $Q_{c2}=0$, that is, when the cold-end is adiabatic, the maximum temperature difference in theory is reached. When the cold-end temperature $T_c$ is constant, no matter how the temperature of the hot-end changes, the applied current to get the maximum temperature difference is the same, and the current value equals to the current value of the maximum cooling capacity. Therefore, based on the Imax~$T_c$ curve which is drawn according to test result of method 1, the optimal current at different cold-end temperatures can be obtained by the interpolation method. Therefore, the test method for maximum cooling temperature difference is: setting the cold-end as $T_C$, and fixing the output of the constant current source at Imax ($T_C$), changing the temperature of the hot-end to make $Q_C$ close to 0, and determining the temperature difference at this time to be the maximum cooling temperature difference.

Second Embodiment

Figure 6:
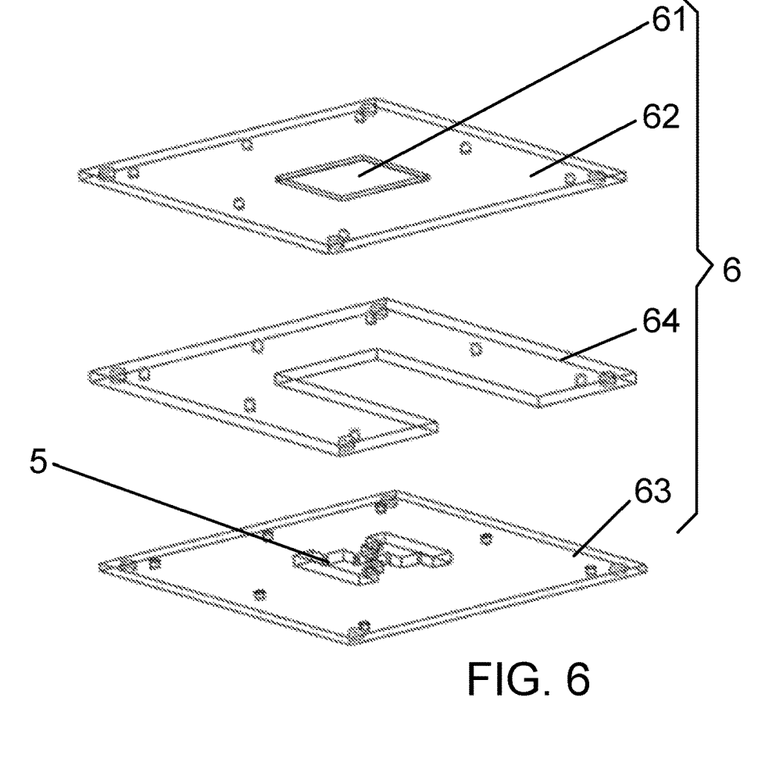
FIG. 6 shows the structure schematic diagram of the heat flux guide unit of the second embodiment of the invention.

In this embodiment, the test system also includes a heat flux guide unit 6 arranged between the cold-end of the thermoelectric module 2 and the first plane.

Heat flux guide unit 6 is used to guide the heat flux at the cold end of the thermoelectric module 2 after flowing through the heat flux sensor 5 to flow directly to the first temperature control unit 41 substantially without loss to surrounding area. Heat flux guide unit 6 effectively avoids the loss of heat flux, and makes all the heat flux of the cold-end of the thermoelectric module 2 flows through the heat flux sensor 5. With the heat flux guide unit 6, the difference between the heat flux detected by heat flux sensor 5 and the true heat flux is substantially reduced and the precision of the testing system is improved.

As shown in FIG. 6, the heat flux guide unit 6 includes a heat conducting sheet 61 and a first heat insulation plate 62. The heat conducting sheet 61 is installed between the cold-end of the thermoelectric module and the heat flux sensor 5. The first heat insulation plate 62 is disposed between the thermoelectric mode and the heat flux sensor 5. A containing groove of the heat conducting sheet is set in the first heat insulation plate 62. The heat conducting sheet 61 is arranged in the containing groove of the heat conducting sheet.

In the embodiment, the depth of the containing groove is ⅔ of the first heat insulation plate 62. The first heat insulation plate plays a role of avoiding the loss of heat flux to surrounding area of the heat conductive sheet. It is advantageous to improve the measurement precision of the heat flux of the thermoelectric module 2.

The containing groove of the heat conducting sheet is set in the surface of the first heat insulation sheet 62 with the back to the thermoelectric module 2. The heat conducting sheet contacts with the heat flux sensor 5. The heat conducting sheet transfers the heat flux of the cold-end of the thermoelectric module 2 to the heat flux sensor 5.

It can also be preferably that the heat flow guide unit 6 comprises a heat conducting sheet 61 and a first heat insulation plate 62. The heat conducting sheet 61 is arranged between the cold-end of the thermoelectric module and the heat flux sensor 5. A containing hole of the heat conducting sheet is set in the first heat insulation plate 62. The heat conducting sheet 61 is arranged in the containing hole of the heat conducting sheet.

By setting the heat conducting sheet 61 in the containing hole of the heat conducting sheet on the first heat insulation plate 62, the first heat insulation plate plays a role of avoiding the loss of heat flux around the heat conducting sheet. It is good to reduce the difference between the heat flux detected by heat flux sensor 5 and the true heat flux, and improve the testing precision of the testing system.

The heat flux guide unit 6 also includes a heat conducting plate 63 arranged between the first plane and the first heat insulation plate 62. The heat flux sensor 5 is set between the heat conducting plate 63 and the heat conducting sheet 61.

The first surface of the heat conducting plate 63 contacts the first plane of the first temperature control unit 41. The second surface of the heat conducting plate 63 contacts the thermoelectric module. The area of heat conducting plate 63 is larger than that of the heat flux sensor. Therefore, the heat conducting plate 63 is beneficial to transfer the heat flux passing through the heat flux sensor 5 to the first temperature control unit 41. Further, it is beneficial to keep the temperature of the cold-end of the thermoelectric module consistent with the temperature of the first temperature control unit.

The heat flux guide unit 6 also includes the second heat insulation plate 64 which is arranged between the first heat insulation plate 62 and the heat conducting plate 63, containing through-hole matched with the heat flux sensor 5 is set on the second heat insulation plate 64.

The heat flux sensor 5 is arranged on the containing through-hole of the second heat insulation plate 64, which effectively avoids the loss of the heat flow, and further improves the measuring precision of the test system.

The sensor containing groove used to contain the heat flux sensor 5 is arranged on the surface of the heat conducting plate 61 towards the heat conducting plate 63. The heat flux sensor 5 is arranged in the sensor containing groove. The containing groove is used for fixing the heat flux sensor 5 to prevent the heat flux sensor 5 from moving with respect to the heat conduction plate 63.

The depth of the sensor containing groove is less than the thickness of the heat flux sensor 5; heat flux guide unit 6 also includes the second heat insulation plate 64 which is arranged between the first heat insulation plate 62 and the heat conducting plate 63, containing through-hole matched with the heat flux sensor 5 is set on the second heat insulation plate 64 in order to accommodate the part of the heat flux sensor 5 which is higher than the containing groove of the sensor.

The second heat insulation plate 64 is used to prevent the loss of the heat flux of the part of the heat flux sensor 5 which is higher than the containing groove of the sensor, further improves the precision of the heat flux detected by the heat flux sensor 5 and increases the testing precision of the testing system.

The above is only the preferred embodiment of the invention, and should not be used to limit the invention; for the technical personnel in the field, the invention can have various changes and variations. In the spirit and principle of the invention, any modification, equivalent replacement or improvement, etc., shall be included in the protection scope of the invention.

What is claimed is:

1. A test system for testing a thermoelectric module, the test system comprising:
   a test platform including a first temperature control unit having a first plane and a second temperature control unit having a second plane, the second temperature control unit being controllably movable in a direction substantially perpendicular to the first plane;
   an electrical performance test unit electrically connected with the thermoelectric module with a cold-end of the thermoelectric module attached to the first plane at a cold-end-temperature controlled by the first temperature control unit and a hot-end of the thermoelectric module attached to the second plane at a hot-end-temperature controlled by the second temperature control unit, and configured to measure an output power of the thermoelectric module, and working current and internal resistance under the output power;
   a heat flux detection unit including at least one heat flux sensor installed between the cold-end of the thermoelectric module and the first plane to detect a heat flux at the cold-end; and a processor electrically connected with the electrical performance test unit to receive information measured by the electrical performance test unit and connected with the heat flux detection unit to receive the heat flux for calculating thermoelectric conversion efficiency based on the information associated with the output power, the working current, the internal resistance, and the heat flux.

2. The test system of claim 1, wherein the test platform comprises a thermal-conductive material plate including a first surface configured to be attached with the first plane and a second surface configured to be attached with the cold-end of the thermoelectric module, the second surface comprising a groove structure configured to hold the at least one heat flux sensor therein substantially matched in size.

3. The test system of claim 1, wherein the heat flux detection unit comprises multiple heat flux sensors disposed in a same level between the cold-end and the first plane, the multiple heat flux sensors being all in rectangular shape with various lengths in parallel to a first symmetry axis of the thermoelectric module and substantially being laid in mirror symmetric locations relative to the first symmetry axis, the farther being a heat flex sensor away from the first symmetry axis the larger being the length of the heat flex sensor.

4. The test system of claim 3, wherein the multiple heat flux sensors comprises a central one having dimensions of 10×10 mm, two having dimensions of 30×8 mm located in two mirror symmetric positions separated from the central one by 2 mm, and additional two having dimensions of 50×8 mm located in two outer mirror symmetric positions separated from the two previous ones by 2 mm.

5. The test system of claim 1, wherein the test platform comprises a supporting plate configured to support the first temperature control unit by fixedly attaching to a bottom of the first temperature control unit separated by a first heat-insulating material layer, the bottom being aft plane opposite to the first plane.

6. The test system of claim 5, wherein the test platform comprises a heat-insulating material disposed to surround the peripheral side of the thermoelectric module between the first temperature control unit and the second temperature control unit.

7. The test system of claim 1, further comprising a heat flux guide unit disposed between the cold-end of the thermoelectric module and the first plane for guiding the heat flux, after flowing through the at least one heat flux sensor, to flow toward the first temperature control unit substantially in a direction perpendicular to the first plane.

8. The test system of claim 7, wherein the heat flux guide unit comprises a first insulating plate having a hole for setting a heat conducting sheet leveled with a first surface of the first insulating plate, the heat conducting sheet being in contact with the at least one heat flux sensor, the first surface of the first insulating plate being in contact with the cold-end of the thermoelectric module.

9. The test system of claim 8, wherein the heat flux guide unit further comprises a second insulating plate having a hole for accommodating the at least one heat flux sensor therein and a heat conducting plate disposed between a second surface of the first insulating plate and the first plane, the heat conducting plate being in contact with the at least one heat flux sensor.

10. The test system of claim 1, wherein the test platform includes a driving unit configured to drive the second temperature control unit to move in the direction perpendicular to the first plane, the driving unit includes a fixture part including a horizontal member having a threaded hole and two vertical members having respective guided rails fixedly set with respect to the first temperature control unit and a driving screw rod configured to move forward through the threaded hole for pressing the second temperature control unit to clamp the thermoelectric module between the second temperature control unit and the first temperature control unit.

11. The test system of claim 10, wherein the driving screw rod through the threaded hole comprises a hole diameter of about 50 mm for providing up to 800 kg clamping force and a thread pitch of 0.5 mm for yielding an error of less than 10 µm for a thread-in motion of the driving screw rod for clamping the thermoelectric module between the second temperature control unit and the first temperature control unit.

12. The test system of claim 10, wherein the driving unit comprises a transmission part including a first moving plate coupled with an end region of the driving screw rod via bearings and coupled with the two vertical members via two pulleys in the respective guided rails for transferring pressure from a rotation motion of the driving screw rod to a vertical motion of the first moving plate substantially friction free and to keep the whole transmission part rotational free.

13. The test system of claim 12, wherein the transmission part comprises a second moving plate coupled with the first moving plate via an elastic fixture and fixedly attached to the second temperature control unit separated by a second insulating material layer.

14. The test system of claim 13, wherein the elastic fixture comprises a plurality of connecting screws surrounded partially by a plurality of springs respectively disposed through the first moving plate to connect to the second moving plate at multiple positions for adjusting clamping force thereof for tuning parallelism of the second plane relative to the first plane with the thermoelectric module held therebetween for substantially maximizing the output power.

\* \* \* \* \*